US00PP30267P2

(12) United States Plant Patent
Eveleens

(10) Patent No.: US PP30,267 P2
(45) Date of Patent: Mar. 5, 2019

(54) *HYDRANGEA* PLANT NAMED 'HORTMAGIBO'

(50) Latin Name: *Hydrangea macrophylla*
Varietal Denomination: Hortmagibo

(71) Applicants: KOLSTER HOLDING B.V., Boskoop (NL); HORTEVE BREEDING B.V., Aalsmeer (NL)

(72) Inventor: Cornelis P. Eveleens, Aalsmeer (NL)

(73) Assignees: Kolster Holding B.V., Boskoop (NL); Horteve Breeding B.V., Aalsmeer (NL)

( * ) Notice: Subject to any disclaimer, the term of this patent is extended or adjusted under 35 U.S.C. 154(b) by 0 days.

(21) Appl. No.: 15/731,886

(22) Filed: Aug. 21, 2017

(51) Int. Cl.
*A01H 5/02* (2018.01)

(52) U.S. Cl.
USPC ..... Plt./250
CPC ..... *A01H 5/02* (2013.01)

(58) Field of Classification Search
USPC ..... Plt./250
See application file for complete search history.

(56) References Cited

PUBLICATIONS

UPOV hit on *Hydrangea* plant named 'Hortmagibo', QZ PBR 20163250 filed Dec. 22, 2016.*
EU PBR application, Feb. 15, 2017, Horteve Breeding B.V.

* cited by examiner

*Primary Examiner* — Anne Marie Grunberg
(74) *Attorney, Agent, or Firm* — C. A. Whealy

(57) ABSTRACT

A new and distinct cultivar of *Hydrangea* plant named 'Hortmagibo', characterized by its upright to broadly spreading plant habit; moderately vigorous growth habit and moderate growth rate; freely branching habit with strong and thick sturdy stems; mophead-type inflorescences with dark red purple-colored sterile flowers; and good postproduction longevity.

2 Drawing Sheets

Botanical designation: *Hydrangea macrophylla.*
Cultivar denomination: 'HORTMAGIBO'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'Hortmagibo'.

The new *Hydrangea* plant is a product of a planned breeding program conducted by the Inventor in Boskoop, The Netherlands. The objective of the breeding program was to create new *Hydrangea* plants with large inflorescences with numerous dark red purple-colored sterile flowers and good postproduction longevity.

The new *Hydrangea* plant originated from a cross-pollination made by the Inventor on Jun. 10, 2010 in Boskoop, The Netherlands, of a proprietary selection of *Hydrangea macrophylla* identified as code number 08-036-07, not patented, as the female, or seed, parent with *Hydrangea macrophylla* 'Erm-1', not patented, as the male, or pollen, parent. The new *Hydrangea* plant was discovered and selected by the Inventor as a single flowering plant from within the progeny of the stated cross-pollination in a controlled greenhouse environment in Boskoop, The Netherlands in July, 2014.

Asexual reproduction of the new *Hydrangea* plant by vegetative terminal cuttings in a controlled environment in Boskoop, The Netherlands has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Hortmagibo'. These characteristics in combination distinguish 'Hortmagibo' as a new and distinct *Hydrangea* plant:

1. Upright to broadly spreading plant habit.
2. Moderately vigorous growth habit and moderate growth rate.
3. Freely branching habit with strong and thick sturdy stems.
4. Mophead-type inflorescences with dark red purple-colored sterile flowers.
5. Good postproduction longevity.

Plants of the new *Hydrangea* can be compared to plants of the female parent selection. Plants of the new *Hydrangea* differ primarily from plants of the female parent selection in sterile flower color as sterile flower sepals of plants of the female parent selection are pink and green in color. In addition, inflorescences of plants of the new *Hydrangea* are more globular than and not as flat as inflorescences of plants of the female parent selection.

Plants of the new *Hydrangea* can be compared to plants of the male parent, 'Erm-1'. Plants of the new *Hydrangea* differ primarily from plants of 'Erm-1' in sterile flower color as plants of 'Erm-1' have darker colored sterile flower sepals. In addition, sterile flowers of plants of the new *Hydrangea* are more durable than sterile flowers of plants of 'Erm-1'.

Plants of the new *Hydrangea* can be compared to plants of the *Hydrangea macrophylla* 'Kolmaru', disclosed in U.S. Plant Pat. No. 25,104. In side-by-side comparisons plants of the new *Hydrangea* differ primarily from plants of 'Kolmaru' in the following characteristics:

1. Plants of the new *Hydrangea* have slightly smaller inflorescences than plants of 'Kolmaru'.
2. Plants of the new *Hydrangea* have more durable sterile flowers than plants of 'Kolmaru'.
3. Plants of the new *Hydrangea* and 'Kolmaru' differ in sterile flower color as plants of 'Kolmaru' have darker red purple-colored sterile flower sepals.

Plants of the new *Hydrangea* can also be compared to plants of the *Hydrangea macrophylla* 'Glowing Alps', not patented. In side-by-side comparisons plants of the new *Hydrangea* differ primarily from plants of 'Glowing Alps' in the following characteristics:

1. Plants of the new *Hydrangea* have stronger lateral branches than plants of 'Glowing Alps'.
2. Plants of the new *Hydrangea* have more durable sterile flowers than plants of 'Glowing Alps'.
3. Plants of the new *Hydrangea* and 'Glowing Alps' differ in sterile flower color as plants of 'Glowing Alps' have dark pink-colored sterile flower sepals.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'Hortmagibo'.

The photograph on the second sheet is a close-up view of a typical inflorescence of 'Hortmagibo'.

DETAILED BOTANICAL DESCRIPTION

Plants used in the aforementioned photographs and in the following description were grown during the late spring in 17-cm containers in a glass-covered greenhouse in Boskoop, The Netherlands and under cultural practices typical of commercial *Hydrangea* production. During the production of the plants, day temperatures ranged from 18° C. to 25° C. and night temperatures ranged from 16° C. to 17° C. Plants of the new *Hydrangea* were two years old when the photographs and description were taken. Plants of the new *Hydrangea* are not typically treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'Hortmagibo'.

Parentage:

*Female, or seed, parent.*—Proprietary selection of *Hydrangea macrophylla* identified as code number 08-036-07, not patented.

*Male, or pollen, parent.*—*Hydrangea macrophylla* 'Erm-1', not patented.

Propagation:

*Type cutting.*—By vegetative terminal cuttings.

*Time to initiate roots, summer.*—About three weeks at temperatures about 15° C. to 25° C.

*Time to produce a rooted young plant, summer.*—About six weeks at temperatures about 15° C. to 25° C.

*Root description.*—Medium in thickness, fibrous; typically creamy white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Upright and broadly spreading plant habit; overall plant shape is flattened globular; strong and sturdy lateral branches; moderate growth rate and moderately vigorous growth habit.

*Plant height.*—About 48 cm.

*Plant diameter or area of spread.*—About 65.2 cm.

Lateral branch description:

*Branching habit.*—Freely branching habit; when pinched, about 18 lateral branches develop per plant.

*Length.*—About 22.2 cm.

*Diameter.*—About 6.5 mm.

*Internode length.*—About 5.1 cm.

*Texture.*—Smooth, glabrous; fully developed, woody.

*Aspect.*—Upright to about 32.5° from vertical.

*Strength.*—Strong, sturdy.

*Color.*—When developing: Close to 144A. Developed: Close to 144A; at the internodes, tinged with close to 178A; when woody, close to 199A and 199B.

*Lenticels.*—Density: Dense. Length: About 2 mm. Diameter: About 0.5 mm. Color: Close to N186C.

Leaf description:

*Arrangement.*—Opposite, simple.

*Length.*—About 10.3 cm.

*Width.*—About 8.2 cm.

*Shape.*—Ovate to roughly broadly elliptic.

*Apex.*—Apiculate.

*Base.*—Obtuse.

*Margin.*—Serrate.

*Texture, upper surface.*—Smooth to moderately rugose, glabrous.

*Texture, lower surface.*—Smooth to moderately rugose, surface mostly glabrous, however small tufts of short hairs present at vein axils.

*Venation pattern.*—Pinnate.

*Color.*—Developing leaves, upper surface: Close to 144A. Developing leaves, lower surface: Close to between 143B and 144A. Fully expanded leaves, upper surface: Darker than between NN137A and 147A; venation, close to 143C. Fully expanded leaves, lower surface: Close to 147B; venation, close to 146C.

*Petioles.*—Length: About 1.3 cm. Diameter: About 3.5 mm. Texture and luster, upper surface: Smooth, glabrous; glossy. Texture and luster, lower surface:

Smooth, glabrous; moderately glossy. Color, upper surface: Close to 144B. Color, lower surface: Close to 144A.

Flower description:

*Flower type and habit*.—Showy sterile flowers and small inconspicuous fertile flowers arranged on mophead-type terminal panicles; panicles globular and slightly flattened in shape; fertile flowers face mostly upright and sterile flowers face upright to outwardly and slightly drooping depending on their position in the inflorescence.

*Fragrance*.—None detected.

*Natural flowering season*.—Plants flower from late spring to late summer in The Netherlands.

*Flower longevity*.—Fertile flowers last about one week on the plant, fertile flowers not persistent; sterile flowers last about six weeks on the plant, sterile flowers persistent.

*Quantity of flowers*.—Freely flowering habit; about 35 fertile flowers per panicle and about 165 sterile flowers per panicle.

*Panicle height*.—About 10.7 cm.

*Panicle diameter*.—About 16.2 cm.

*Fertile flower buds*.—Length: About 6 mm. Diameter: About 4 mm. Shape: Obovate. Color: Close to 63B and 63C; towards the base, close to 145B.

*Sterile flower buds*.—Length: About 3 mm. Diameter: About 3 mm. Shape: Globular. Color: Close to 64D.

*Fertile flower diameter*.—About 9 mm.

*Fertile flower depth* (*height*).—About 8 mm.

*Sterile flower diameter*.—About 4.4 cm.

*Sterile flower depth* (*height*).—About 1.6 cm.

*Petals, fertile flowers*.—Quantity and arrangement: Four or occasionally five in a single whorl. Length: About 4 mm. Width: About 2.5 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to N66C and N66D. When opening and fully opened, lower surface: Close to 63B.

*Petals, sterile flowers*.—Quantity and arrangement: About four in a single whorl. Length: About 4 mm. Width: About 2.5 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to N66C and N66D. When opening and fully opened, lower surface: Close to 63B.

*Sepals, fertile flowers*.—Quantity and arrangement: About four in a single whorl. Length: About 1.5 mm. Width: About 1.5 mm. Shape: Ovate. Apex: Acute. Base: Broadly cuneate. Margin: Entire. Texture and luster, upper and lower surfaces: Smooth, glabrous; matte. Color: When opening, upper and lower surfaces: Close to 59D. Fully opened, upper and lower surfaces: Close to 59D; towards the apex, close to 146D; color does not change with development.

*Sepals, sterile flowers*.—Quantity and arrangement: Four or occasionally three in a single whorl. Length: About 2.6 cm. Width: About 3.1 cm. Shape: Broadly reniform to rhomboidal and broadly ovate. Apex: Bluntly and broadly acute. Base: Cuneate. Margin: Irregularly dentate to serrate. Texture and luster, upper and lower surfaces: Smooth, glabrous; matte. Color: When opening, upper surface: Close to between N57B and 58B. When opening, lower surface: Close to N57C to N57D. Fully opened, upper surface: Close to between 58A and 59B; towards the margins, close to 58B; color becoming closer to 183B with development. Fully opened, lower surface: Close to 59D and lighter than 59D; color becoming closer to 182B with development.

*Pedicels, fertile flowers*.—Length: About 3 mm. Diameter: About 1 mm. Strength: Moderately strong. Aspect: Mostly upright, about 15° from vertical. Texture and luster: Smooth, glabrous; matte. Color: Close to 63C to 63D.

*Pedicels, sterile flowers*.—Length: About 1.9 cm. Diameter: About 1.5 mm. Strength: Moderately strong. Aspect: About 40° from vertical. Texture and luster: Moderately pubescent; matte. Color: Close to 64D.

*Reproductive organs, fertile flowers*.—Stamens: Quantity per flower: About eight. Filament length: About 4 mm. Filament color: Close to 65B. Anther length: About 1 mm. Anther shape: Oblong. Anther color: Close to 156A to 156B. Pollen amount: Moderate. Pollen color: Close to 159D. Pistils: Pistil quantity per flower: About two or occasionally three. Pistil length: About 1 mm. Stigma shape: Club-shaped. Stigma color: Close to NN155C. Style length: About 0.6 mm. Style color: Close to 65D. Ovary color: Close to 150D and lighter than 150D.

*Reproductive organs, sterile flowers*.—Stamens: Quantity per flower: About eight. Filament length: About 3 mm. Filament color: Close to 65C. Anther length: About 1 mm. Anther shape: Oblong. Anther color: Close to 155C. Pollen amount: Moderate. Pollen color: Close to 159D. Pistils: Pistil quantity per flower: About two. Pistil length: About 1 mm. Stigma shape: Club-shaped. Stigma color: Close to NN155C. Style length: About 0.6 mm. Style color: Close to 65D. Ovary color: Close to 157D.

*Seeds*.—Seed development has not been observed on plants of the new *Hydrangea* to date.

Disease & pest resistance: Under commercial production conditions, plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 to 9.

It is claimed:

1. A new and distinct *Hydrangea* plant named 'Hortmagibo' as illustrated and described.

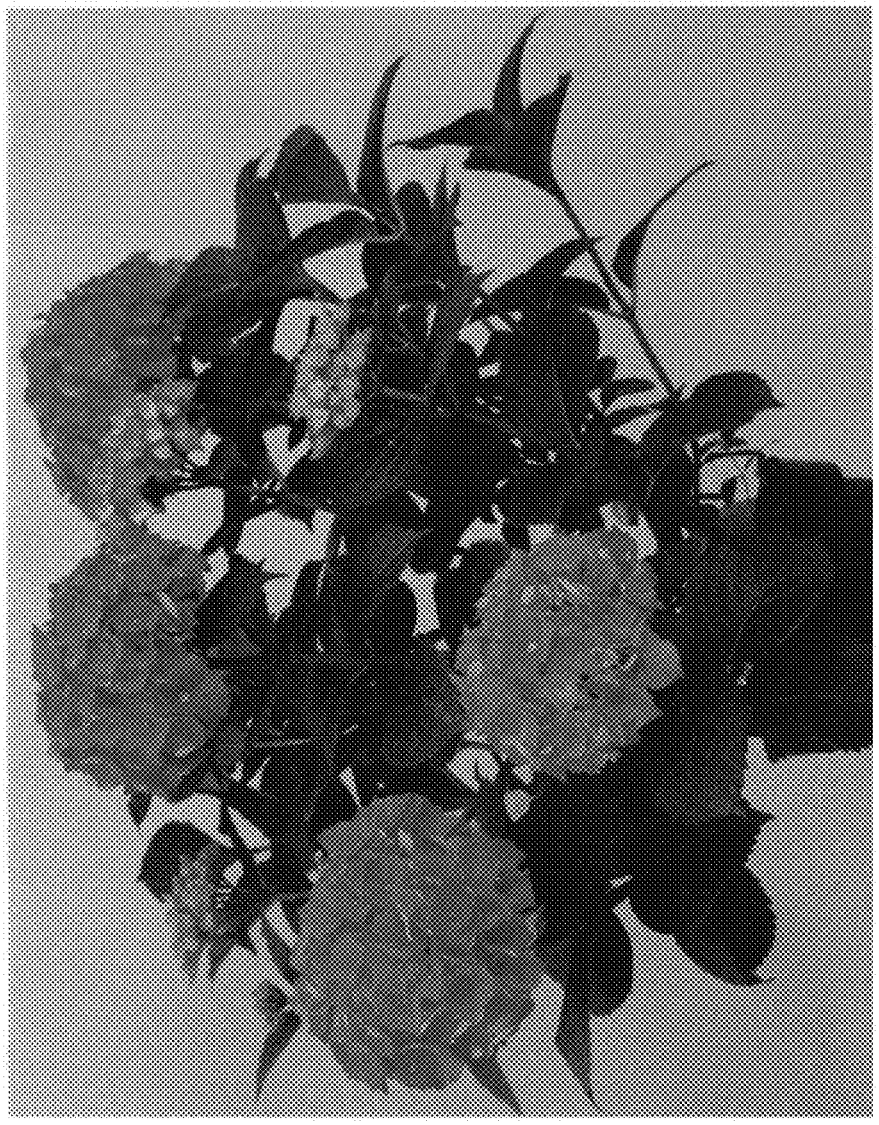

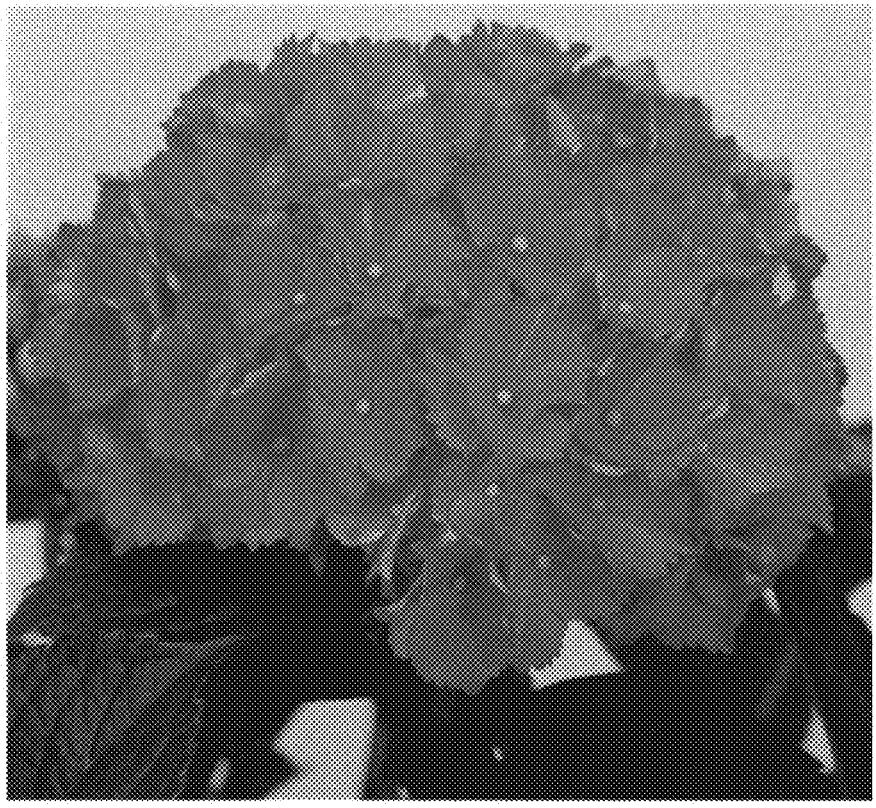

* * * * *